United States Patent [19]

Yoneda et al.

[11] Patent Number: 4,801,541
[45] Date of Patent: Jan. 31, 1989

[54] METHOD OF INCREASING THE YIELD OF A PRODUCT BY ALTERING A MICROORGANISM

[75] Inventors: Yuko Yoneda, Rochester; Frank E. Young, Pittsford, both of N.Y.

[73] Assignee: The University of Rochester, Rochester, N.Y.

[21] Appl. No.: 58,688

[22] Filed: Jun. 3, 1987

Related U.S. Application Data

[63] Continuation of Ser. No. 519,911, Aug. 3, 1983, abandoned, which is a continuation of Ser. No. 301,417, Sep. 11, 1981, abandoned.

[51] Int. Cl.$^4$ .................. C12N 15/00; C12N 9/28; C12N 1/20; C12R 1/125
[52] U.S. Cl. ......................... 435/172.3; 435/172.1; 435/202; 435/320; 435/839; 435/252.31; 935/14; 935/38; 935/39; 935/43; 935/61; 935/74
[58] Field of Search ............... 435/68, 70, 71, 172.1, 435/172.3, 202, 253, 839, 317.1, 320; 935/14, 38, 39, 43, 72, 74, 61; 536/27

[56] References Cited

PUBLICATIONS

Bergey's Manual of Systematic Bacteriology, vol. 1, (Krieg et al., ed.)., 1984, Williams & Wilkins, Baltimore, p. 2.
Biochem. Biphys. Res. Comm., 31(2):182–187 (1968), S. Yuki "On the Gene Controlling the Rate of Amylase Production in *Bacillus subtilis*".
*J. Bacteriol.*, 111:705–716 (1972), G. A. Wilson et al. "Intergenotic Transformation of the *Bacillus subitlis* Genospecies".
*Gene*, 7:51–68 (1971), Y. Yoneda, et al. "Restriction—Fragment Map of the Temperature *Bacillus subtilis* Bacteriophage SPO2".
*J. Virol.*, 20:509–519 (1976), D. H. Dean, et al. "New Temperate Bacteriophage for *Bacillus subtilis*, p. 11".
*J. Bacteriol.*, 121:354–362 (1975), T. Tanaka, et al. "Construction of a Colicin El-R Factor Composite Plasmid in vitro: Means for Amplification of Deoxyribonucleic Acid".
*Biochem. Biophys. Res. Comm.*, 18:788–795 (1965), E. A. Adelberg, et al. "Optimal Conditions for Mutagenesis by N-Methyl-N'-Nitro-N-Nitro-soguanidine in *Escherichia coli* K12".
*J. of Virol.*, 14:1013–1016 (1974), G. A. Wilson, et al. "Characterization of Temperature Bacteriophages of *Bacillus subtilis* by the Restriction Endocnuclease EcoRI: Evidence for Three Different Temperature Bacteriophages".
*J. Gen. Virol.*, 4:489–504 (1969), R. G. Tucker "Acquisition of Thymidylate Synthetase Activity by the Thymine-Requiring Mutant of *Bacillus subtilis* following Infection by the Temperate Phage 03".
*J. of Virol.*, 21:522–529 (1977), M. T. Williams, et al. "Temperate *Bacillus subtilis* Bacteriophage 03T: Chromosomal Attachment Site and Comparison with Temperature Bacteriophages 015 and SPO2".
*Biochim. Biophys. Acta*, 72:619–629 (1963), H. Saito, et al. "Preparation of Transforming Deoxyribonucleic Acid by Phenol Treatment".
*Proc. Nat. Acad. Sci.*, 65(1):206–213 (1970), H. Yoshikawa, "Temperature-Sensitive Mutants of *Bacillus subtillis*, I, Multiforked Repliction & Sequential Transfer of DNA by a Temperature-Sensitive Mutant".
*Transformation*–1980, Cotswold Press Ltd., Oxford, UK (1981), Y. Yoneda, et al "Cloning of Genes of Industral Importance in *Bacillus subtilis* Model System: Synergistic Effects . . . ".

Primary Examiner—James Martinell
Attorney, Agent, or Firm—Martin LuKacher

[57] ABSTRACT

A method is described for increasing the yield of a product from a microorganism containing a regulatory gene, by altering the microorganism. The method involves introducing into the microorganism at least one structural gene for the product by lysogenizing the microorganism with a recombinant bacteriophage containing the structural gene.

7 Claims, No Drawings

METHOD OF INCREASING THE YIELD OF A PRODUCT BY ALTERING A MICROORGANISM

This is a continuation of application Ser. No. 519,911 filed Aug. 3, 1983 which was a continuation of application Ser. No. 301,417 filed Sept. 11, 1981, both now abandoned in favor of the present application.

BACKGROUND OF THE INVENTION

1. Field of the Invention

Microbial enzymes are becoming increasingly important in such diverse fields as medicine, agriculture and organic chemicals production. The genus Bacillus comprises a group of bacteria that can be easily maintained and cultivated, yet are markedly heterogeneous in character. All of the 48 species of the Bacillus genus listed in Bergey's *Manual of Determinative Bacteriology* secrete soluble enzymes.

The microorganism *B. subtilis* offers numerous advantages for industrial processes and has been used for decades in industrial fermentations that yield amylase, proteases and other products.

Some of the advantages of *B. subtilis* include the production of various proteins (extracellular) which are completely dissociated from the cell and found free in the surrounding medium, raising the possibility of altering such microorganism to produce commercial fermentation products. In addition, *B. subtilis* does not survive in or on vertebrates and has not been shown to produce any serious human illness.

It is well known that the genetic information of all cells is stored in deoxyribonucleic acid (DNA) in the chromosomal material of microorganisms. The unit of genetic function, i.e., the locus on the chromosome related to a specific hereditary trait, is called a gene.

Prior to the advent of recombinant DNA technology, gene studies and genetic manipulations have been carried out by the classical genetic techniques of transformation and transduction. Recombinant DNA technology involves the transfer of genetic material (genes, or DNA fragments) from one organism into a second organism, by means of a transfer component designated a "vector", producing a combination of genetic material. The second organism (which contains the transferred genetic material) is designated a recombinant component. The recombinant component can then be used as a source of DNA to insert genetic material into bacterial and animal cells for propagation of the combined genes contained in the recombinant component. The cell into which the DNA of the recombinant component is inserted is designated a host cell.

Using recombinant DNA technology, genetic modification can be accomplished as follows. Specific DNA fragments from a vector, e.g., a lysogenic bacteriophage are "isolated", e.g., by treatment with appropriate restriction enzymes which act as "chemical scalpels" to split DNA molecules into specific fragments which usually contain from less than 1 to 10 genes each, or by other well known techniques. A DNA fragment for the desired genetic characteristic, i.e., "foreign DNA" from the bacterial source is then inserted into the DNA bacteriophage vector. By treatment with DNA ligase the DNA fragment is inserted into the bacteriophage DNA vector and a recombinant bacteriophage DNA molecule is formed. The recombinant bacteriophage contains all or most of the genes of the bacteriophage plus the new genes (foreign DNA) from the inserted fragment. This recombinant bacteriophage can be introduced into a host bacterium thereby "cloning" the foreign DNA into the host. The new genes are propagated and become a part of the genetic machinery of the bacterium host. If successful, the bacterium host thus acquires the gentic traits contributed by the new genes and is capable of "expressing" these traits.

2. Prior Art

Previous studies have established that the level of α-amylase synthesis in *B. subtilis* is regulated by a number of genes. Studies have indicated that α-amylase is regulated by a specific regulatory gene (amyR) that can be linked to its structural gene (amyE) by transformation. [See *J. Bacteriol.* 119: 410–415 (1974); *J. Gen. Appl. Microbiol.,* 15: 97–107 (1969) and *Biochem. Biophys. Res. Commun.,* 31: 182–187 (1968)]. In addition to production of α-amylase attributed to the amyE and amyR genes, α-amylase production can be achieved by a "pleiotrophic" mutation, i.e., by a gene that regulates more than one function. Known pleiotrophic mutations include the papM gene ("production of α-amylase and protease") and a gene designated tmr encoding resistance to the antiviral antibiotic tunicamycin; both these genes are regulatory genes.

It is known that genes according or regulating α-amylase in a Bacillus strain can be introduced into *B. subtilis* if the two strains are sufficiently closely related, i.e., if there is extensive genetic homology between the two strains. This is referred to as homologous transformation. For example, *J. Bacteriol.,* 120: 1144–1150 (1974) describes the introduction of DNA from *B. subtilis* var *amylosacchariticus* having exceptionally high α-amylase activity, into a genetically similar (homologous) microorganism having relatively low α-amylase activity (*B. subtilis* Marburg). The transformed microorganisms which were produced acquired high α-amylase activity.

However, most Bacillus are not sufficiently related to *B. subtilis,* i.e., are not sufficiently homologous, to permit the DNA obtained from one *Bacillus subtilis* strain to be efficiently introduced into a different Bacillus strain. *J. Bacteriol.,* 111: 705–716 (1972).

*Appl. Environ. Microbiol.* 39: 274–276 (1980) established that the effect of incorporating the related genes (amyR3, amyS, papS1, tmr and papM118) into a strain produced an increase in α-amylase production of a synergistic nature. The overall approach involved the stepwise introduction of the amy, pap and tmr genes into a recipient *B. subtilis* Marburg 6160 (a *B. subtilis* 168) microorganism by a stepwise transformation procedure. The authors indicate that because the transformation procedure requires chromosomal homology, a suggested alternative approach which can utilize chromosomal heterology would involve the development of vectors for cloning the genes and introducing them into a modified recipient, i.e., a "mother cell" in a more purified form.

Although the regulatory genes from *Bacillus natto* and *Bacillus subtilis* var. *amylosacchariticus* can be introduced readily into homologous *B. subtilis* 168 by DNA-mediated transformation, it is extraordinarily difficult to use such conventional transformation techniques in a heterologous transformation, e.g., to introduce genes from *B. amyloliquefaciens* into *B. subtilis* 168. As indicated in *J. Bacteriol.,* 111: 705–716 (1972), particularly Table 2, transformation of a *B. subtilis* 168 strain (BR151) with DNA from a homologous *B. subtilis* 168 strain produced one thousand-fold more transformants for three tested loci than DNA from a heterologous source, *B. amyloliquefaciens H.*

*Biochem. Biophys. Res. Comm.*, 91: 1556-1564 (1979) describes a method of cloning heterologous genes in bacteriophage φ3T, producing a specialized transducing bacteriophage containing the genetic information encoding α-amylase from *B. amyloliquefaciens H.*

However, while the above paper predicts that the use of such a technique will allow the insertion of a variety of Bacillus genes encoding extracellular enzymes into *B. subtilis* it is not predictable whether regulatory genes inserted into the *B. subtilis* will also function to regulate or enhance the production of α-amylase encoded by a foreign (i.e., heterologous) cloned gene.

SUMMARY OF THE INVENTION

The present invention is directed to a method of increasing the yield of a product by a microorganism. The method involves introducing in a host microorganism, containing a regulatory gene capable of regulating the biosynthesis of the product, at least one structural gene for the product. The structural gene is introduced by lysogenizing the host microorganism with a recombinant bacteriophage containing the structural gene. Alternatively, the method involves introducing into the host microorganism at least one regulatory gene capable of regulating the biosynthesis of the product and introducing at least one structural gene for said product by lysogenizing the host microorganism with a recombinant bacteriophage containing the structural gene.

DETAILED DESCRIPTION OF THE INVENTION

The method of the present invention is suitable for increasing the yield of diverse products produced by microorganisms. Such products include extracellular enzymes, intracellular enzymes, antibiotics and metabolic products. Extracellular enzymes include α-amylases, proteases, celluloses, hemicellulase, penicillinases and pectinases. Intracellular enzymes include lytic enzymes, glucose isomerase, polynucleotide phosphorylase, restriction endonucleases and dextranases. Antibiotics include edeine $A_1$ and $B_1$, bacitracin A, gramicidin A, tyrocidine, butirosin and 1-desoxyinojirimycin. Metabolic products include vitamins, cofactors, amino acids, nucleotides and polysaccharides.

Research has established that the function of regulatory genes is to regulate the biosynthesis of products by the microorganism. Structural genes encode the information for the biosynthesis, and in effect serve as a "template" for the product. The structural gene itself is often comprised of regulatory components that can also regulate a low level of biosynthesis, i.e., a "base level". Insertion of a regulatory gene, if successful, can increase the "base level" biosynthesis of the structural gene product.

The identity of the regulatory genes suitable for use in the present invention is not critical, nor is the identity of the structural genes. Regulatory genes suitable for use in increasing biosynthesis of α-amylase include amyR and papM. Other regulatory genes include sacU, promoters and operator sequences.

Structural genes suitable for use in increasing biosynthesis of α-amylase include φ3T-amy+. Other structural genes include those encoding amylases or starch hydrolyzing proteins from other microorganisms.

The regulatory gene can be present in a parent host, can be inserted by conventional techniques, or can be produced in a host by mutation. One or more regulatory genes and one or more structural genes can be used in the present invention, in order to construct a "mother strain", with increased biosynthetic capability. If a regulatory gene is inserted into a host microorganism, the regulatory gene can be inserted either before or after lysogenization with the recombinant bacteriophage.

The Examples describe the use of φ3T bacteriophage. Other suitable bacteriophages include SP02 [See *Gene*, 7: 51-68 (1971)] and Rho11 (ρ11) [See *J. Virol.*, 20: 509-519 (1976)].

The method for producing the recombinant bacteriophage is described hereinafter [See *Biochem. and Biophys. Res. Comm.*, 91: 1556-1564 (1979)].

The method for producing the recombinant bacteriophage involves first obtaining chromosomal DNA encoding the desired product from a microorganism, digesting with an appropriate restriction enzyme, e.g., an enzyme isolated from *B. globigii* (Bgl II) to cleave the DNA, and inactivating the enzyme. The DNA from a bacteriophage is similarly treated with a restriction enzyme and the enzyme inactivated. The DNA from the microorganism and from the bacteriophage are then ligated by known techniques to produce a ligated mixture of DNA consisting of recombinant molecules. The recombinant molecule mixture contains randomly ligated mixtures of chromosomal DNA fragments, bacteriophage fragments and chromosomal fragments linked to bacteriophage fragments. [See *J. Bacteriol.*, 121: 354-362 (1975)].

The mixture of recombinant DNA molecules is incubated with DNA isolated from a second microorganism and with a third microorganism that serves as the recipient. The second microorganism does not contain the genetic fragment to be incorporated and is substantially genetically homologous with the recipient microorganism. The concept of homologous and heterologous microorganisms, is well-known and discussed in *J. Bacteriol.*, 111: 705-716 (1972). In addition, the second microorganism differs from the recipient in that it has a selectable trait.

The step of incubating the host microorganism with DNA isolated from a second microorganism which is substantially genetically homologous and which has a selectable trait is a technique for selecting recipient microorganisms which can react with DNA and therefore provide enrichment for transformed microorganisms. This is an example of a widely used genetic technique. In some bacterial strains, a means for "primary" selection exists, e.g., if the transformed bacteria is resistant to a certain antibiotic the bacteria can be cultured in the presence of such antibiotic and the cells which survive can be selected as viable transformants. This process, involving genes which are vital to the survival of the bacteria, is designated primary selection and involves the use of a "selectable trait". Selectable traits are not limited to the antibiotic resistance referred to above, but include growth characteristics. The present embodiment described in Example I utilizes homologous DNA prototrophic for a growth requirement, i.e., threonine (Thr+) and a recipient Bacillus microorganism auxotrophic for threonine (Thr−). The identity of the auxotrophic growth requirement is not critical. Growth requirements for other amino acids or purines or pyrimidines could be used with the appropriate microorganism as well as such selective traits as antibiotic resistance. For example, suitable amino acids include lysine, tyrosine, alanine, leucine and serine. Suitable purines and pyrimidines include adenine, thymine, guanine, cytosine and uracil. Antibiotic resistant traits include resistance to erythromycin, spectinomycin and streptomycin.

In contrast, some genetic transformants do not confer a selectable trait, e.g., genetic traits which are not vital or do not contribute to the survival of the bacteria under stressed or selective conditions, e.g., production of extracellular enzymes such as α-amylase, proteases, cellulases and hemicellulases. Approximately one percent or less of the cells in the population are capable of being transformed. Thus the primary selection technique is not essential to arrive at the transformed cell, but constitutes a preferred embodiment.

However, these transformants can be determined by means of biochemical tests. This technique is referred to as screening. In order to determine which of the recombinant bacteriophages incorporated in the transformed microorganisms contain the desired structural gene, the transformed microorganisms must be screened. One method of screening for a transformant which does not involve a selectable trait is by use of a biochemical test as described further below. In the present example, the transformed microorganisms are screened for the production of α-amylase by a conventional starch-iodine test. The recombinant bacteriophage can then be obtained from the transformed microorganisms by inducing the transformed microorganisms.

The desired structural gene, carried in the recombinant bacteriophage, is introduced into the host microorganism by lysogenizing the host with the recombinant bacteriophage. Lysogenization can be defined as a process of bacteriophage infection, whereby the genetic material of the bacteriophage forms a stable association with the host microorganism. Not all bacteriophage are capable of this alternative association and the usual mode of infection results in production of bacteriophage and death of the microorganisms. This usual "lytic" response can be "induced" in a stable lysogen by a variety of chemical or physical treatments.

In the following Examples, various microorganisms are designated as having an ATCC number. Each microorganism so designated is available from the American Type Culture Collection, Rockville, Md.

EXAMPLE I

Bacterial cultures of a *B. subtilis* strain designated *B. subtilis* Marburg 6160, a derivative of *B. subtilis* 168, having the genotype purB6, metB5, trpB3, proL, amyR1, amyEm, described in *J. of Bacteriol.*, 119: 410–415 (1974), were maintained by growing the cultures in a bouillon-yeast extract media containing the following components per liter of distilled water:bouillon, 5 g; yeast extract, 2 g; polypeptone, 10 g; and NaCl, 2 g. The pH was adjusted to 7.2 by addition of NaOH. *B. subtilis* 6160 is available from the personal collection of Dr. Frank E. Young, The University of Rochester, Rochester, N.Y.

*B. subtilis* 6160 was first mutated into *B. subtilis* 6160-1 as described in *J. Bacteriol.*, 124: 48–54 (1975), by treatment with ultraviolet radiation. The ultraviolet radiation technique involved shining ultraviolet light on the *B. subtilis* 6160 microorganisms. After ultraviolet radiation treatment, the microorganisms were grown in the above bouillon-yeast extract media. The mutant selected was designated *B. subtilis* Marburg 6160-1 and had the following genotype: purB6, metB5, trpB3, proL, amyR1, amyEm, str, where str indicates streptomycin resistance.

As indicated hereinafter in Table I, *B. subtilis* produces small amounts of *subtilis*-type (S-type) α-amylase. To select mutants with a higher α-amylase production, α-amylase productivity was determined by measuring the halo around the colony grown on a bouillon-yeast agar plate, as described below.

To isolate mutants, the *B. subtilis* microorganisms were grown in the above medium to 100 to 150 Klett units at 37° C., centrifuged and washed with 0.05M tris(hydroxymethyl)aminomethane-malate buffer. Sterile N-methyl-N'-nitro-N-nitrosoguenidine was added to a final concentration of 100 μg/ml as described in *Biochem. Biophys. Res. Commun.*, 18: 788–795 (1965). The cells were collected on a membrane filter, washed and suspended in the bouillon-yeast medium to give the same volume of original cell suspension. Glycerol was added to the cell suspension to a final concentration of 20 percent, and the cell suspension was stored in liquid nitrogen. Frozen cells were melted quickly and grown at 37° C. for three hours in bouillon-yeast medium. The culture was diluted with and plated on bouillon-yeast-agar medium containing 1 percent soluble starch, and KI-I$_2$ solution (0.01M) was sprayed on the colonies grown on the plate after an overnight incubation at 37° C. Colonies with a large unstained halo around them, indicating increased α-amylase production, were selected.

Mutants having increased α-amylase production capacity, were selected as described above and were designated *B. subtilis* Marburg YN9, having the following genotype: purB6, metB5, trpB3, proL, amyR1, amyEm, str, papM9, indicating that the regulatory gene papM was present.

Colonies of YN9 mutants were maintained by standard procedures, and their synthesis of S-type α-amylase determined, as described hereinafter.

Colonies of YN9 mutants were then lysogenized with a bacteriophage carrying a heterologous α-amylase structural gene from *B. amyloliquefaciens H*. The α-amylase structural gene was inserted into the bacteriophage as follows.

A. Preparation and Isolation of α-amylase Structural Gene (*B. amyloliquefaciens* DNA)

Chromosomal DNA encoding an α-amylase structural gene, amyE+ was obtained from *B. amyloloquiefaciens H* RUB 500 (ATCC 31592) as described below. [See *J. Virol.*, 14: 1013–1016 (1972)].

*B. amyloliquefaciens H* was grown in 50 to 100 ml of a peptone medium commercially available from Difco Laboratories, Detroit, Mich. under the trade designation Difco Penassay Broth. After about 18 hours of incubation with shaking at 37° C., the cells were harvested by centrifugation and washed twice and suspended in 10 ml of a buffer which consisted of 0.15M tris(hydroxymethyl)aminomethane hydrochloride buffer, commercially available from Sigma Chemical, St. Louis, Mo. under the trade designation Trizma Base and 0.1M ethylenediamine tetraacetic acid (EDTA) at a pH of 8.0. The cell suspension was centrifuged again and lysed by suspending it in 5 ml of the above buffer solution, which additionally contained crystalline egg white lysozyme (1 mg per ml) for 30 minutes at 37° C. An enzyme to degrade protein, (1 mg/ml) was added and the culture was incubated at 50° C. for 10 minutes and then at 37° C. for 50 minutes. A suitable enzyme is available from Calbiochem. LaJolla, Calif. under the trade designation Pronase. The cytoplasmic membrane protein complex was removed from the DNA by treatment with a mixture of detergents made up of sodium lauryl sulfate and a detergent commercially available from Ciba-Geigy Corporation, Ardsley, N.Y., under the trade designation Sarkosyl NL-97. The detergent final concentration was about 2 percent weight/volume composed of equal parts of the above detergents.

Incubation was continued at 50° C. until total dissociation of the cytoplasmic membranes occurred. The DNA was then extracted three times using redistilled phenol saturated with a buffer made of 0.1M Trizma Base at a pH of 8.0. The DNA was precipitated by the addition of 0.1M NaCl with 10 ml cold 95 percent ethanol, wound on a glass rod, washed in three successive 70 percent ethanol solutions and dissolved in 10 mM Trizma Base containing 1 mM EDTA, at a pH of 7.5. The DNA was stored at 4° C. over chloroform.

The isolated DNA was then digested with the restriction enzyme Bgl II to hydrolyze the DNA. Bgl II is commercially available from Miles Laboratories, Inc., Elkhart, Ind., and is isolated from the microorganism *B. globigii*. The Bgl II enzyme was then inactivated by heating the mixture to 60° C. for 15 minutes.

B. Preparation and Isolation of φ3T Bacteriophage

The bacteriophage used was φ3T, first isolated by Tucker as described in *J. Gen. Virol.*, 4: 489–504 (1969). The φ3T used was obtained by growing bacteria strain RUB 830 (φ3T) as described below. RUB 830 (φ3T) has been described earlier [*J. Virol.*, 21: 522–529 (1977)], and is available from the personal collection of Wilson and Young, University of Rochester.

High titers of φ3T were obtained by growing RUB 830 (φ3T) in a growth medium (designated M) at 32° C. to a density of 50 Klett units (Klett-Summerson Colorimeter, filter no. 66) and inducing with mitomycin C (final concentration, 0.5 μg/ml) and concentrating the bacteriophage by centrifugation or precipitation with $(NH_4)_2SO_4$. M medium contained: 10 gm of a pancreatic digest of casein commercially available from Difco Laboratories, Detroit, Mich. under the trade designation Bacto-Tryptone; 5 gm yeast extract; 9.9 gm NaCl; and 1,000 ml distilled water. The mixture was autoclaved and a sterile solution of 5 ml of 1M $MgCl_2$ and 0.1M $MnCl_2$ added.

The DNA of φ3T bacteriophage was isolated according to the procedure used to isolate DNA from *B. amoliquefaciens H* and then digested with Bgl II restriction enzyme to hydrolyze the DNA. The Bgl II enzyme was then inactivated by heating the mixture to 60° C. for 15 minutes.

The DNA from *B. amyloliquefaciens H* and φ3T were combined and ligated as described below. [See *J. Bacteriol.*, 121: 354–362 (1975)].

C. Ligation Procedure

The ligase reaction was carried out in a final volume of 100μ liters. The DNA isolated from *B. amyliquefaciens H* and the φ3% bacteriophage were mixed together, placed on ice and the following added: 50 mM MgCl (10μ liters); 0.1M dithioerythritol (10μ liters); 0.5 mM adenosine triphosphate (10μ liters); water (20μ liters); and DNA ligase (1 U/mg DNA). The reaction mixture was incubated on ice for 12 hours at 14° C.

The ligated mixture containing recombinant molecules was incubated with chromosomal DNA from a second *B. subtilis* microorganism homologous to the recipient but prototrophic for a growth requirement for which the recipient Bacillus is auxotrophic. 100μ liter of the mixture containing the recombinant molecules from C above was incubated with 100 μl (1 μg) of *B. subtilis* RUB 200 (ATCC 31593) DNA. RUB 200 is a strain that is prototrophic for threnonine (Thr+) and defective in α-amylase biosynthesis (Amy−).

D. Transformation and Selection of Recombinant Bacteriophage

The entire mixture from above (200μ liters) was incubated with 100μ liters of a recipient competent strain of *B. subtilis* RUB 201, (ATCC 31594). The recipient RUB 201 is auxotrophic for threonine (Thr−) and lysogenic for bacteriophage φ3T (as explained later). The incubation was carried out at 37° C. for 0.5 hour with aeration.

Samples (0.1 ml) of the incubated host were spread on plates of Spizizen's minimal agar (supplemented with 22 mM glucose, 20 μg/ml of each of the aromatic amino acids, tryptophan; phenylalanine; tyrosine and 1 percent soluble starch, but not containing threonine) in order to select for cells transformed to threonine independence (Thr+). Cells which were transformed from Thr− to Thr+, i.e., threonine independence have been transformed by incorporating DNA. Out of these cells, a certain number will have also taken up DNA fragments which include the α-amylase gene (amy+) and be transformed into α-amylase producing transformants.

Approximately $10^5$ cells were obtained which were viable in the absence of threonine. Cells which had not been transformed to Thr+ were not viable in the absence of threonine and did not survive. The transformants were then screened for α-amylase production by the technique described earlier. The *B. subtilis* RUB 201 was transformed into *B. subtilis* RUB 204 (ATCC 31595) which contains the recombinant bacteriophage of φ3T which has incorporated the α-amylase structural gene amy+. *B. subtilis* RUB 204 has the genotype: aroI, trpB2, thr+, (φ3T-amy+), amyE−.

The YN9 strain was then lysogenized with recombinant φ3T bacteriophage prepared from *B. subtilis* RUB 204 (ATCC 31495-B1) containing recombinant φ3T bacteriophage, i.e., the α-amylase structural gene amy+.

The lysogenization was accomplished as described in *J. Virol.*, 21: 522–529 (1977), by growing the YN9 strain to a density of about $10^8$ Colony Forming Units/ml in a peptone medium, commercially available friom Difco Laboratores, Detroit, Mich., under the trade designation Difco Penassay Broth. The recombinant bacteriophage (φ3T-amy+) from *B. subtilis* RUB 204 was added at a multiplicity of infection of 1.

As described earlier, in lysogenization, the genome of the bacteriophage forms a stable association with the chromosome of the cell which is infected, i.e., the host chromosome. This stabilized genome containing cell is resistant to bacteriophage infection. An alternate occurrence is that the bacteriophage will infect the microorganism, synthesize bacteriophage and cause the cell to burst and release bacteriophages. Occasionally a stable genome-containing cell is derepressed and bursts and releases bacteriophage which in turn kill surrounding non-infected cells, leaving a group of lysogenized cells (plaque) surrounded by a clear "halo".

The plaque sizes of the lysogenized cells in the center of the "halo" were distinguished on tryptose blood agar base plates in an overlay containing the desired bacterial indicator, i.e., the uninfected host cells, 2 ml of M medium containing 10 gm of a pancreatic digest of casein commercially available from Difco Laboratories, Detroit, Mich. under the trade designation Bactotryptone;

5 gm of yeast extract; 9.9 gm NaCl; and 1,000 ml distilled water. The mixture was autoclaved and a sterile solution of 5 ml of 1M $MgCl_2$ and 0.1M $MnCl_2$ added. A clear "halo" around the infectious center indicated that the infected cells had been lysogenized by the recombinant bacteriophage. This procedure converted strain YN9 into a strain designated as RUB 236 carrying the structural α-amylase gene, having the genotype: purB, metB, trpB, papM, str, amyE+, amyR1, φ3T-amy+.

To determine whether the α-amylase regulatory gene does regulate α-amylase produced by the α-amylase structural gene inserted from the heterologous source, i.e., from *B. amyloliquefaciens H*, and thus increase the α-amylase production of the *B. subtilis* host microorganism, the amount of α-amylase of H-type and S-type was measured, by immunological means described below. [See *J. Bacteriol.*, 119: 410–415 (1974)].

The immunological differentiation between S-type and H-type α-amylase is based on the principle that antibodies from S-type α-amylase can neutralize ("inactivate") S-type α-amylase, but no H-type α-amylase. Conversely, antibodies from H-type α-amylase can neutralize H-type α-amylase, but not S-type α-amylase. The immunological method involves obtaining S-type and H-type antibodies, adding either type antibodies to the α-amylase to be tested, and determining the enzyme activity remaining. The procedure is then repeated with the other type antibodies.

Serum containing S-type antibodies was prepared as follows. A mixture of S-type α-amylase, obtained from Seikagaku Kogyo Co., Tokyo, Japan, (9.6 mg in 0.5 ml 85 percent NaCl) and 0.5 ml complete Freund adjuvant was injected subcutaneously into a rabbit. Two weeks later the rabbit received an additional subcutaneous injection of the S-type α-amylase adjuvant mixture (5.9 mg α-amylase). Blood samples were obtained two weeks after the second injection. The serum was separated, incubated at 56° C. for 30 minutes to inactivate complement and stored at 20° C. The S-type anti-amylase serum was diluted with 0.85 percent NaCl solution. A similar procedure was followed to obtain serum containing H-type anti-amylase antibodies using H-type α-amylase prepared from *B. amyloliquefaciens*.

Bacteriol cells of *B. subtilis* 6160, YN9 and RUB 236 were grown overnight with aeration in bouillon-yeast medium at 30° C. and each culture diluted 100-fold with fresh bouillon-yeast. The microorganisms were cultivated for 24–30 hours at 30° C. when the maximal activity of the enzyme was reached. Each culture was chilled in an ice bath and centrifuged at 6,000×g for 10 minutes to remove the cells. The supernatant fluid was used as a crude α-amylase enzyme solution. When necessary to concentrate the α-amylase, the enzyme solution was brought to 50 percent saturation with ammonium sulfate and the precipitate containing the α-amylase was dissolved in 0.04M phosphate buffer (pH 6.0). The α-amylase was used after extensive dialysis against the same buffer at 4° C.

A 0.5 ml sample of the α-amylase from *B. subtilis* 6160, YN9 and RUB 236 respectively, was mixed with the same volume of S-type anti-amylase, incubated at 40° C. for 30 minutes and centrifuged at 6,000×g for 15 minutes. The neutralization was complete after this period of time. The procedure was repeated with H-type anti-amylase.

The α-amylase activity was assayed by adding a 2 ml portion of 0.5 percent soluble starch in a phosphate buffer (pH 6.0) to 1 ml of the α-amylase enzyme solution that had been treated with anti-S or anti-H antibodies. Nontreated α-amylase enzyme solution was used as a control and similarly assayed. After incubation at 40° C., a 0.2 ml sample of each reaction mixture was added to separate 5 ml portions of 0.00017M $I_2$-KI solution. The optical density at 700 mμ was spectrophotometrically measured. Hydrolysis of 0.1 mg of soluble starch in 1 minute was defined as 1 Unit of α-amylase activity.

The experimental results obtained are summarized in Table I below.

TABLE I

| Strain | Relevant Genotype | α-amylase (Units/ml) | | |
|---|---|---|---|---|
| | | S-Type | H-Type | Total |
| Parent *B. subtilis* 6160 | purB, metB, trpB, amyE+, amyR1 | 11.0 | NT* | 11.0 |
| YN9 | purB, metB, trpB, amyE+, amyR1, papM, str | 32.8 | NT | 32.8 |
| RUB 236 | purB, metB, trpB, amyE+, amyR1, papM, str, φ3T-amy+ | 48.1 | 682.7 | 734.9 |

*NT denotes not detected.

The data above indicate that the parent *B. subtilis* Marburg 6160 produced a small amount of subtilis-type α-amylase. Mutation of the parent 6160 strain to incorporate the regulatory papM gene increased the synthesis of S-type α-amylase from 11.0 to 38.2 Units. Lysogenization with recombinant bacteriophage produced from the *B. subtilis* RUB 204 containing an α-amylase structural gene was successful, as indicated by the production of 682.7 U of H-type α-amylase, indicating that the regulatory papM gene can regulate and increase not only the α-amylase produced by the amyE+ gene (S-type) as shown by the increase in S-type α-amylase in YN9, but can also regulate the inserted foreign (heterologous) structural gene, i.e., the φ3T-amy+ from the bacteriophage.

EXAMPLE II

*B. subtilis* 6160 was used as the parent strain and transformed by conventional techniques into *B. subtilis* SP3866 by DNA obtained from *B. subtilis* SP38. [See *Appl. and Environ. Micro.*, 39: 274–276 (1980)]. DNA from the SP38 strain used in the transformation procedure was extracted by the method described in *Biochem. Biophys. Acta*, 72: 619–620 (1963). The procedures used in the transformation procedure were those described in *Proc. Nat. Acad. Sci.*, U.S.A., 65: 206–213 (1970). After obtaining SP3866, the SP3866 strain was lysogenized with recombinant φ3T bacteriophage prepared from *B. subtilis* RUB 204 as described in Example I, to convert SP3866 into a strain designated as RUB 240 carrying the φ3T-amy+ structural α-amylase gene. The amount of S-type and H-type α-amylase was determined by the immunological test described in Example I. The experimental results obtained are summarized in Table II below.

TABLE II

| Strain | Relevant Genotype | α-amylase (Units/ml) | | |
|---|---|---|---|---|
| | | S-Type | H-Type | Total |
| Parent *B. subtilis* 6160 | purB, metB, trpB, amyE+, amyR1 | 11.0 | NT | 11.0 |
| *B. subtilis* SP3866 | purB, metB, trpB, amyS, str, amyE+, amyR1 | 44.8 | NT | 44.8 |
| *B. subtilis* RUB240 | purB, metB, trpB, amyS, str, amyE+, amyR1, | 208.6 | 126.7 | 352.8 |

TABLE II-continued

| Strain | Relevant Genotype | α-amylase (Units/ml) | | |
|---|---|---|---|---|
| | | S-Type | H-Type | Total |
| | φ3T-amy+ | | | |

The data above indicate that the parent *B. subtilis* Marburg 6160 produced a small amount of subtilis-type α-amylase. Mutation of the parent 6160 strain to incorporate the regulatory amyS gene increased the synthesis of S-type α-amylase from 11.0 to 44.8 Units. Lysogenization with recombinant bacteriophage produced from the *B. subtilis* RUB 204 containing an α-amylase structural gene was successful, as indicated by the production of 126.7 U of H-type α-amylase, indicating that the regulatory amyS gene can regulate and increase not only the α-amylase produced by the amyE+ gene (S-type) as shown by the increase in S-type α-amylase in SP3866, but can also regulate the inserted foreign (heterologous) structural gene, i.e., the φ3T-amy+ from the bacteriophage.

EXAMPLE III

*B. subtilis* 6160 was used as the parent strain and transformed by conventional techniques into *B. subtilis* SP44 by DNA obtained from *B. subtilis* var amylosaccharticus. After obtaining *B. subtilis* SP44, the SP44 was lysogenized with recombinant φ3T bacteriophage prepared fom *B. subtilis* RUB 204, as described in Example I, to convert SP44 into a strain designated as *B. subtilis* RUB 237 carrying the φ3T-amy+ structural α-amylase gene. The amount of of H-type and S-type α-amylase was determined by the immunological test described in Example I. The experimental results obtained are summarized in Table III below.

TABLE III

| Strain | Relevant Genotype | α-amylase (Units/ml) | | |
|---|---|---|---|---|
| | | S-Type | H-Type | Total |
| Parent *B. subtilis* 6160 | purB, metB, trpB, amyE+, amyR1 | 11.0 | NT | 11.0 |
| *B. subtilis* SP44 | purB, metB, trpB, papS, amyE+, amyR1 | 26.0 | NT | 26.0 |
| *B. subtilis* RUB 237 | purB, metB, trpB, papS, amyE+, amyR1, φ3T-amy+ | 36.1 | 726.9 | 751.0 |

The data above indicate that the transformation of the parent 6160 strain to incorporate the regulatory papS gene increased the synthesis of subtilis-type α-amylase from 11.0 to 26.0 Units. Lysogenization with recombinant bacteriophage prepared from the *B. subtilis* RUB 204 containing the α-amylase structural gene was successful, as indicated by the production of 726.9 U H-type α-amylase, indicating that the regulatory papS gene can regulate and increase not only the α-amylase produced by the amyE+ gene, but can also regulate the inserted foreign structural gene, i.e., the φ3T-amy+ from the bacteriophage.

A series of experiments similar to the previous experiments was carried out, except that the parent *B. subtilis* 6160 strain was first transformed into a strain which was deficient in α-amylase production, due to the presence of the mutation amyE07. These experiments demonstrated that the regulatory genes can enhance the biosynthesis of α-amylase from a foreign gene in the absence of a homologous functional gene for S-type α-amylase.

EXAMPLE IV

*B. subtilis* RUB 219 was transformed by conventional techniques, as described in Example II, into *B. subtilis* RUB 212 by DNA from strain YN118 [See *J. Bacteriol.*, 124: 48–54) (1975)]. After obtaining RUB 212, the 212 strain was lysogenized with recombinant φ3T bacteriophage prepared from *B. subtilis* RUB 204 as described in Example I, to convert RUB 212 into a strain designated as RUB 213 carrying the φ3T-amy+ structural α-amylase gene. The amount of S-type and H-type α-amylase was determined by the immunological test described in Example I. The experimental results obtained are summarized in Table IV below.

TABLE IV

| Strain | Relevant Genotype | α-amylase (Units/ml) | | |
|---|---|---|---|---|
| | | S-Type | H-Type | Total |
| Parent *B. subtilis* 6160 | purB, metB, trpB, amyE+, amyR1 | 11.0 | NT | 11.0 |
| *B. subtilis* RUB 202 | aroI, purB, metB, trpB, papM, amyE07, amyR1 | 0.56 | — | 0.56 |
| *B. subtilis* RUB 213 | aroI, purB, metB, trpB, papM, amyE07, amyR1, φ3T-amy+ | Not Determined | 1516.1 | 1516.1 |

The experimental results indicate that regulation of foreign genes is not dependent on the presence of the host structural gene (amyE+) for increasing the yield of the desired α-amylase product.

EXAMPLE V

*B. subtilis* RUB 219 was transformed by conventional techniques, as described in Example II, into *B. subtilis* RUB 214 by DNA from strain SP44. After obtaining RUB 214, the 214 strain was lysogenized with recombinant φ3T bacteriophage prepared from *B. subtilis* RUB 204 as described in Example I, to convert RUB 214 into a strain designated as RUB 215 carrying the φ3T-amy+ structural α-amylase gene. The amount of S-type and H-type α-amylase was determined by the immunological test described in Example I. The experimental results obtained are summarized in Table V below.

TABLE V

| Strain | Relevant Genotype | α-amylase (Units/ml) | | |
|---|---|---|---|---|
| | | S-Type | H-Type | Total |
| Parent *B. subtilis* 6160 | purB, metB, trpB, amyE+, amyR1 | 11.0 | NT | 11.0 |
| *B. subtilis* RUB 214 | aroI, purB, metB, trpB, papS, amyE07, amyR1 | 0.0 | — | 0.0 |
| *B. subtilis* RUB 215 | aroI, purB, metB, trpB, papS, amyE07, amyR1, φ3T-amy+ | ND | 1010.7 | 1010.7 |

As in Example IV, the experimental results inicate that regulation of foreign genes is not dependent on the presence of the host structural gene (amyE+) for increasing the yield of the desired α-amylase product.

What is claimed is:

1. A method for increasing the yield of α-amylase in a *Bacillus subtilis* host microorganism which comprises introducing into said host at least one regulatory gene capable of increasing the biosynthesis of said α-amylase and introducing into said host nicroorganism at least one structural gene for said α-amylase from a heterologous microorganism by lysogenizing said host microorganism with a recombinant bacteriophage containing said structural gene wherein the combination of said introduced regulatory gene and structural gene results in a rate of biosynthesis of α-amylase that exceeds a base level amount produced in said *Bacillus subtilis* in the absence of said introduced combination.

2. A method as claimed in claim 1 wherein said recombinant bacteriophage is produced by:
   (a) obtaining genetic fragments encoding the biosynthesis of said α-amylase from said heterologous microorganism;
   (b) isolating DNA fragments from a bacteriophage;
   (c) ligating the genetic fragments obtained in step (a) with the DNA fragments obtained in step (b) to produce a mixture containing a series of recombinant molecules;
   (d) incubating the mixture of step (c) with DNA isolated from a second microorganism which does not contain said genetic fragments obtained in step (a), said second microorganism having substantial genetic homology with said host microorganism and having a selectable trait;
   (e) incubating the mixture of step (d) with said recipient third microorganism, said recipient third microorganism being lysogenic for said bacteriophage of step (b) and deficient in said selectable trait to produce a mixture containing a transformed third microorganism which is altered for said selectable trait, and lysogenic for said desired recombinant bacteriophage and which contains genes encoding the biosynthesis or regulation of said α-amylase;
   (f) selecting said transformed third microorganism by growing said mixture on a selective medium which does not allow microorganisms to grow that are deficient in said selectable trait and determining biosynthesis of said α-amylase; and
   (g) obtaining therefrom said recombinant bacteriophage containing genes encoding the biosynthesis of said α-amylase by inducing said transformed third microorganism.

3. A method for increasing the yield of α-amylase in a *Bacillus subtilis* host microorganism which comprises the steps of introducing at least one regulatory gene capable of increasing the biosynthesis of α-amylase and introducing at least one structural gene for α-amylase wherein the combination of said introduced regulatory gene and structural gene results in a rate of biosynthesis of amylase that exceeds a base level amount produced in said *Bacillus subtilis* in the absence of said introduced combination by lysogenizing said *Bacillus subtilis* with a recombinant bacteriophage produced by:
   (a) obtaining genetic fragments encoding synthesis of α-amylase;
   (b) isolating DNA fragments from a bacteriophage;
   (c) ligating the genetic fragments obtained in step (a) with the DNA fragments obtained in step (h) to produce a mixture containing a series of recombinant molecules;
   (d) incubating the mixture of step (c) with DNA isolated from a second Bacillus microorganism which does not contain said genetic fragments obtained in step (a), said second Bacillus microorganism having substantial genetic homology with a third Bacillus microorganism and being prototrophic for a growth requirement;
   (e) incubating the mixture of step (d) with said third *Bacillus subtilis* microorganism, said Bacillus being lysogenic for said bacteriophage of step (b) and auxotrophic for said growth requirement to produce a mixture containing a transformed third *Bacillus subtilis* microorganism which is prototrophic for said growth requirement, lysogenic for said desired recombinant bacteriophage and which contains said α-amylase structural gene within said bacteriophage; and
   (f) selecting said transformed third *Bacillus subtilis* microorganism which does not contain said growth requirement and determining the presence of said α-amylase structural gene, and obtaining therefrom said recombinant bacteriophage containing said α-amylase structural gene by inducing said prototrophic transformed third Bacillus microorganism.

4. A method as claimed in claim 3 wherein the genetic fragments of (a) are obtained from Bacillus DNA.

5. A method as claimed in claim 4 wherein the Bacillus DNA fragments are obtained from *B. amyloliquefaciens H*.

6. A method as claimed in claim 3 wherein the DNA fragments of (b) are obtained from a Bacillus recombinant bacteriophage.

7. A method as claimed in claim 6 wherein the DNA fragments of (b) are obtained from *B. subtilis* recombinant bacteriophage.

* * * * *